United States Patent [19]
Koermer et al.

[11] Patent Number: 5,948,683
[45] Date of Patent: Sep. 7, 1999

[54] CATALYST FOR SELECTIVE OXIDATION OF UNSATURATED HYDROCARBONS AND METHODS OF MAKING AND USING THE SAME

[75] Inventors: Gerald S. Koermer, Roseland; Ahmad Moini, Princeton, both of N.J.

[73] Assignee: Engelhard Corporation, Iselin, N.J.

[21] Appl. No.: 08/953,871

[22] Filed: Oct. 18, 1997

[51] Int. Cl.$^6$ .................................................. G01N 31/10
[52] U.S. Cl. ........................... 436/37; 436/142; 436/159; 422/177; 502/208; 502/304
[58] Field of Search ............................ 436/37, 142, 159; 422/177; 502/100, 101, 208, 210, 300, 302, 304

[56] References Cited

U.S. PATENT DOCUMENTS

| | | | |
|---|---|---|---|
| 2,435,196 | 2/1948 | Bond et al. | 502/208 |
| 2,449,050 | 9/1948 | Bond et al. | 502/208 |
| 2,865,842 | 12/1958 | Hirschler et al. | 502/210 |
| 3,416,884 | 12/1968 | Stynes et al. | 502/208 |
| 3,442,954 | 5/1969 | Crocker et al. . | |
| 3,598,530 | 8/1971 | Fenske et al. | 436/142 |
| 3,600,331 | 8/1971 | Ingwalson et al. | 502/208 |
| 3,634,286 | 1/1972 | Yates . | |
| 3,682,836 | 8/1972 | Jaffe | 502/210 |
| 3,697,550 | 10/1972 | Bayne et al. | 502/208 |
| 3,733,327 | 5/1973 | Vrieland . | |
| 3,752,878 | 8/1973 | Kehl et al. . | |
| 3,838,182 | 9/1974 | Kehl et al. . | |
| 3,969,273 | 7/1976 | Brown et al. | 502/210 |
| 4,080,311 | 3/1978 | Kehl | 502/208 |
| 4,233,184 | 11/1980 | Cull | 502/210 |
| 4,363,748 | 12/1982 | Crum et al. . | |
| 4,384,985 | 5/1983 | Crum et al. . | |
| 4,751,342 | 6/1988 | Kimble . | |
| 5,118,870 | 6/1992 | Kemp . | |
| 5,260,241 | 11/1993 | Addiego et al. . | |
| 5,278,115 | 1/1994 | Kresge et al. . | |
| 5,278,116 | 1/1994 | Kresge et al. . | |
| 5,310,715 | 5/1994 | Kresge et al. . | |

FOREIGN PATENT DOCUMENTS

| | | |
|---|---|---|
| 257557 | 3/1988 | European Pat. Off. . |
| 327985 | 8/1989 | European Pat. Off. . |
| 435445 | 7/1991 | European Pat. Off. . |
| 562806 | 9/1993 | European Pat. Off. . |
| 2048309 | 4/1972 | Germany . |
| 3630614 | 3/1988 | Germany . |
| 3638010 | 5/1988 | Germany . |
| 3823160 | 1/1990 | Germany . |
| 3826303 | 2/1990 | Germany . |

(List continued on next page.)

OTHER PUBLICATIONS

Diwell, A. F.; Rajaram, R. R.; Shaw, H. A,.; Truex, T. J. "The Role of Ceria in Three–Way Catalysts." Stud. Surf. Sci. Catal. (1991), 71(Catal. Automot. Pollut. Control 2), 139–52, 1991.

(List continued on next page.)

Primary Examiner—Jill Warden
Assistant Examiner—Kevin P. Cannell

[57] ABSTRACT

A selective catalytic material is used to catalyze selective oxidation of unsaturated hydrocarbons, e.g., olefins, in the presence of carbon monoxide. The catalytic material comprises phosphated ceria containing from 0.1 to 20, preferably from 1 to 5, percent by weight phosphate component (calculated as elemental phosphorus). The phosphated ceria may be made by mixing particles of ceria and a solution containing phosphates to disperse the desired amount of phosphate component on the ceria and calcining the particles after separation of them from the solution. The resulting selective catalytic material is contacted under oxidizing conditions with a gas stream containing an oxidant, e.g., air, carbon monoxide and one or more unsaturated hydrocarbons. The selective catalytic material (24a) may be disposed on a sensor (24) disposed within a conduit (18) downstream of a conventional treatment catalyst (16) to evaluate the performance of the latter by measuring the extent of unsaturated hydrocarbon oxidation catalyzed by the selective catalytic material (24a) in the treated gas.

20 Claims, 3 Drawing Sheets

FOREIGN PATENT DOCUMENTS

| | | |
|---|---|---|
| 63-048238 | 2/1988 | Japan . |
| 2072132 | 3/1990 | Japan . |
| 8281116 | 1/1993 | Japan . |
| 6055075 | 3/1994 | Japan . |
| 7070156 | 3/1995 | Japan . |
| 7144134 | 6/1995 | Japan . |
| 7251076 | 10/1995 | Japan . |
| 8169867 | 7/1996 | Japan . |
| 8290061 | 11/1996 | Japan . |
| 498030 | 1/1976 | Russian Federation . |
| 1431868 | 4/1976 | United Kingdom . |
| 9218449 | 10/1992 | WIPO . |
| 9407835 | 4/1994 | WIPO . |
| 9414740 | 7/1994 | WIPO . |

OTHER PUBLICATIONS

Oblicka, M., et al; Ceramic Materials as Carriers of Catalysts For Partial Oxidation of Hydrocarbons; Przemysl Chemiczny, (1971), 50(10), pp. 647–649.

Shimizu, T.; Partial Oxidation of Hydrocarbons and Oxygenated Compounds on Perovskite Oxides; Catal. Rev.— Sci. Eng.; 34(4); 1992; pp. 355–371.

Lunsford, J.H.; The Role of Oxygen Ions in the Partial Oxidation of Hydrocarbons; American Chemical Society Symposium Series; vol. 248 (Catalytic Materials: Relationship Between Structure and Reactivity); 1984; pp. 127–142.

Bartholomé, E.; Development of Processes For Producing Acetylene by Partial Oxidation of Hydrocarbons; Chem.–Ing.–Tech.; 49(1977) Nr. 6 S.; pp. 459–463.

Basevich, V. Ya., et al; Study of Partial Oxidation of Hydrocarbons with Reference to the Production of Synthesis Gas; Theoretical Foundations of Chemical Engineering; vol. 30, No. 5; 1996; pp. 456–460.

Pyatnitskii, Yu. I.; Gas–phase Partial Oxidation of Aromatic Hydrocarbons on Heterogeneous Catalysts; Probl. Kinet. Katal.; vol. 19; 1985; pp. 132–146.

Roberts, J.T., et al; Partial oxidation of hydrocarbons on silver: conversion of 1–butene to maleic anhydride by atomically adsorbed oxygen on Ag(110); Surface–Science 253; 1991; pp. 13–23.

Walsh, D.E., et al; Partial Oxidation of Methane to Liquid Hydrocarbons over ZSM–5 Catalyst; J. Chem. Soc., Chem. Commun.; 1991; pp. 1259–1260.

Gilbert, L., et al; Catalysis by Rare Earth Phosphate II: Selective O–Methylation of Phenols by Methanol in Vapor Phase; Ind. Chem. Libr.; vol. 8; Issue: Roots of Organic Development; 1996; pp. 46–61.

Oh, Soon Jin, et al; Catalytic hydrolysis of phosphate triesters by lanthanide(III) cryptate (2.2.1) complexes; J. Chem. Soc., Perkin Trans. 2; 1995; pp. 329–331.

Hayashi, T., et al; Selective Partial Oxidation of Hydrocarbons over Au/$TiO_2$ Catalysts: Preprints of the American Chemical Society, Div. of Petr. Chem.; vol. 41(1); 1996; pp. 71–74.

Otsuka, K.; Application of Fuel Cell Reaction to Partial Oxidation of Hydrocarbons; Petrotech (Tokyo), vol. 13, No. 12; 1990; pp. 969–973.

Krylov, O.V., et al; Scientific Bases For Improving Catalaysts For Partial Oxidation of Hydrocarbons; The Soviet Chemical Industry, 17:4; (1985); pp. 427–441.

Han, S., et al; Partial Oxidation of Methane to Liquid Hydrocarbons over ZSM–5 Catalyst; Preprints ot the American Chemical Society, Division of Petroleum Chemistry; vol. 37(1); 1992; pp. 61–64.

Shigekawa, H., et al; Core level photoelectron spectroscopy on the lanthanide–induced hydrolysis of DNA; Kidorui; v. 28; Issn: 0910–2205; 1996; pp. 44–45.

Moscotti, D., et al; Catalytic oxydehydrogenation of 2–ethylpyriding; Applied Catalysis A: General 134; 1996; pp. 263–274.

Johnstone, A., et al; Metal Phosphates: New Vistas For Catalysed Oxidations With Hydrogen Peroxide; The Activation of Dioxygen and Homogeneous Catalytic Oxidation; 1993; pp. 45–56.

Tada, Akio, et al; Grinding Effects of Several Phosphates on Their Catalytic Activities; Phosphorus Research Bulletin; vol. 3; 1993; pp. 109–114.

Shiiba, T., et al; Lanthanide metal complexes for the hydrolysis of liner DNAs; Journal of Molecular Catalysis, 84; 1993; pp. L21–L25.

Pemba–Mabiala, J.M., et al; XPS Study of Mixed Cerium–Terbium Orthophosphate Catalysts; Surface and Interface Analysis, vol. 15; 1990; pp. 663–667.

Melikhov, I.V., et al; Certain Features of Crystallization of Cerium (III) Phosphate From Phosphate Solutions; G.V. Plekhanov, Leningrad Mining Institute; pp. 1886–1889; Transalted from Zhurnal Prikladnoi Khimii, vol. 63, No. 9, pp. 2044–2047, Sep. 1990.

Komiyama, M., et al; Consecutive Catalysis by Cerium (III) Ion For Complete Hydrolysis of Phosphodiester Linkage in DNA; Chemistry Express, vol. 8, No. 2; 1993; pp. 85–88.

Martin–Jiménez, F., et al; A highly active silica(silicon)–supported vanadia catalyst for $C_1$ oxygenates and hydrocarbon production from partial oxidation of methane; Catalysis Letters 33; 1995; pp. 279–289.

Bol, C.W.J., et al; Partial oxidation of C1–hydrocarbons on oxygen–covered Rh(111): formaldehyde from methylene; Surface Science 337; 1995; pp. L800–L806.

Jess, A., et al; From Natural Gas to Lipid Hydrocarbons (2) Production of Synthesis Gas by Catalytic Partial Oxidation of Methane with Air; Erdol Erdgas Kohle; vol. 110, No. 9, Issn: 0179–3187; pp. 365–370; Sep. 1994.

Han, S., et al; Direct Partial Oxidation of Methane over ZSM–5 Catalyst: Metals Effects on Higher Hydrocarbon Formation; Journal of Catalysis 148; 1994; pp. 134–137.

Moser, W.R.; Hydrocarbon Partial Oxidation Catalysts Prepared by the High–Temperature Aerosol Decomposition Process Crystal and Catalytic Chemistry; American Chemical Society Symposium Series; vol. 523 (Catalytic Selective Oxidation); 1993; pp. 244–261.

Ozkan, U.S., et al; The partial oxidation of $C_5$ hydrocarbons over vanadia–based catalysts; Catalysis Today 33; 1997; pp. 57–71.

Krylov, O.V.; The Mechanism of the Profound and Mild Oxidation of Hydrocarbons on Transition Metal Oxides; Institute of Chemical Physics; Academy of Sciences of the USSR, Moscow; pp. 24–31; Translated from Kinetika i Kataliz; vol. 14, No. 1; Jan.–Feb. 1973; pp. 35–44.

Krylov, O.V.: et al; Selectivity of partial oxidation of hydrocarbons; Prob. Kinet. Katal. (1985); 19; issn: 0370–0305; pp. 5–28.

Ozkan, U.S., et al; Partial Oxidation of $C_5$ Hydrocarbons to Maleic and Phthalic Anhydrides over Molydate–based Calaysts; Preprints of the American Chemical Society, Division of Petroleum Chem.; vol. 41(1) (1996); pp. 176–178.

Lewis, D.W., et al; Defect processes at low coordinate surface sites of MgO and their role in the partial oxidation of hydrocarbons; Journal of Molecular Catalysis A: Chemical 100; 1995; pp. 103–114.

Andersen, A.G., et al; Preparation and characterization of $CaTiO_3$-based perovskitic osides as catalysts for partial oxidation of light hydrocarbons; Catalysis Letters 18; 1993, pp. 37–48.

Han, S., et al; The Direct Partial Oxidation of Methane to Liquid Hydrocarbons over HZSM–5 Zeolite Catalyst; Journal of Catalysis 136; 1992; pp. 578–583.

Bol, C.W.J.; Partial Oxidation of Hydrocarbons on Rhodium (111); Avail.: Univ. Microfilms Int., Order No. DA9619520; From: Diss. Abstr. Int., B 1996, 57(2), 1101; 269 pp.

Zemanova, Z., et al; Light Microscopic Visualization of Transport ATPase in the Chick Kidney and Intestine Using Catalytic Histochemistry; Acta Histochem. (Jena)96; 1994; pp. 325–334.

Khouw, C.B.; Partial Oxidation of Hydrocarbons Using Titanium Containing Molecular Sieves; Avail: Univ. Microfilms Int., Order No. DA9526833; From: Diss. Abstr. Int., B 1995, 56(4), 2176; 156 pp.

Maksimova, L.G., et al; Synthesis of Series 1:11 Tungsten Heteropoly Complexes with Cerium (IV) and Their Properties; Russian Journal of Inorganic Chemistry; vol. 40, No. 6, 1995: pp. 941–948.

Abstract of: Melikhov, I.V., et al; Some Characteristics of the Crystallization of Cerium (III) Phosphate From Phosphate Solutions; Zh. Prikl. Khim. (Leningrad); 1990; pp. 2044–2047.

Abstract of: Yu, Zhengiang, et al; Oxidative Coupling of Methane Over $Na_2WO_4/CeO_2$ and Related Catalysts; J. Catal.; 1995; pp. 163–173.

Abstract of: Haber, J., et al; Quantum–Chemical Calculations on .Pi.–Allyl Complexes of Cobalt, Nickel, Iron, and Magnesium as an Intermediate in the Selective Oxidation of Propylene; Catal., Proc. Int. Symp.; 1975; Meeting Date 1974; pp. 489–496.

Abstract of: Peacock, John M., et al; Oxidation of Propene Over Bismuth Oxide, Molybdenum Oxide, and Bismuth Molybdate Catalysts, IV, Selective Oxidation of Propene; J. Catal.; 1969; pp. 398–406.

Abstract of: Harrison, Philip G.; The Effect of Calcination on Metal Oxide Oxidation Catalysts; Catal. Today; 1993; pp. 483–491.

Abstract of: Grzybowska, B., et al; Active Centers in Selective Oxidation of Olefins on Molybdate Catalysts; Mech. Hydrocarbon React., Symp.; 1975; Meeting Date 1973; pp. 265–281.

Abstract of: Stroeva, S.S., et al; Investigation of Activity and Selectivity of Some Mixed Catalysts For Selective Oxidation of Unsaturated Hydrocarbons at the C–H Bond; Neftekhimiya; 1996; pp. 412–422.

Abstract of: Ratnasamy, Paul, et al; Selective Oxidation With Redox Metallosilicates in the Production of Fine Chemicals; Stud. Surf. Sci. Catal.; 1995; pp. 367–376.

Abstract of: James, Brian R.; Selective Oxidations With Dioxygen Catalyzed by Ruthenium and Rhodium Complexes; Stud. Surf. Sci. Catal.; 1991; pp. 195–212.

Abstract of: Wolfs, M.W.J., et al; Influence of Preparation and Composition on Multicomponent Molybdate Catalysts For the Selective Oxidation of Olefins; Prep. Catal., Proc. Int. Symp.; 1976; Meeting Date 1975; pp. 161–176.

Abstract of: Kannan, R., et al; Determination of Trace Amounts of Cerium and Thorium by D.C. Polarography; Bull. Electrochem.; 1990; pp. 637–639.

Abstract of: Matyshak, V.A., et al; Surface Compounds Formed During the Catalytic Selective Oxidation of Propylene and Isobutylene; Khim. Fiz. (Moscow); 1984; pp. 1138–1143.

Abstract of: Tada, Akio, et al; Grinding Effects of Several Phosphates on Their Catalytic Activities; Phosphorus Res. Bell.; 1993; pp. 109–114.

Abstract of: Feldhaus, R., et al; Selective Oxidation of C3– and C4– Olefins Over Bismuth Molybdate Catalysts; Geterog. Katal.; 1983, 5th, Pt. 1, pp. 45–49.

Abstract of: Kaneda, Kiyotomi, et al; Highly Selective Oxidation of Allylic Alcohols to Alpha., .Beta.–Unsaturated Aldehydes Using Palladium Cluster Catalysts in the Presence of Molecular Oxygen; J. Org. Chem.; 1996; pp. 4502–4503.

Abstract of: Gilbert, L., et al; Catalysis by Rare Earth Phosphate. II. Selective O–methylation of Phenols by Methanol in Vapor Phase; Industrial Chemical Library; 1996; 8 (Roots of Organic Development); pp. 48–61.

Abstract of: Zemanova, Z., et al; Light Microscopic Visualization of Transport ATPase in the Chick Kidney and Intestine Using Catalytic Histochemistry; Acta Histochem; 1994; pp. 325–334.

Abstract of: Moscotti, D., et al; Catalytic Oxydehydrogenation of 2–Ethylpyridine; Applied Catalysis, A; 1996; pp. 163–74.

Abstract of: Batist, P.A.; The Functions of Redox Couples in Catalysts For the Selective Oxidation of Olefins; Surf. Technol.; 1979; pp. 443–446.

Ishikawa, Toishio, "Partial Oxidation of Hydrocarbons. Oxidation of the Olefin Series Hydrocarbons", Natl. Chem. Lab. Ind., vol. 10, No. 4, (1973), Tokyo, Japan, pp. 223–233.

CATALYST FOR SELECTIVE OXIDATION OF UNSATURATED HYDROCARBONS AND METHODS OF MAKING AND USING THE SAME

BACKGROUND OF THE INVENTION

1. Field of the Invention

The present invention relates to an oxidation catalyst useful for promoting the selective oxidation of unsaturated hydrocarbons, such as olefins, in the presence of carbon monoxide, and to a method of using the catalyst to selectively oxidize such hydrocarbons in the presence of carbon monoxide.

The selective catalytic oxidation of unsaturated hydrocarbons in the presence of carbon monoxide is useful, for example, in treating carbon monoxide-containing gas streams to remove residual unsaturated hydrocarbons, in monitoring the concentration of combustible gases in a given environment, and in gauging the performance of catalysts used to treat exhaust or other waste gas streams, as described below.

2. Related Art

The prior art is aware of the use of vanadium phosphate catalysts for partial oxidation of $C_4$ hydrocarbons, as indicated in an article by V. A. Zazhigalo, of the Inst. Fiz. Khim., Kiev, Ukraine, Katal. Katal. (1992), 28, 3–19.

The use of catalytic metals including alkali metals, alkaline earth metals, rare earth metals and noble metals on porous supports containing zirconium phosphate is known for the treatment of automotive exhaust gas, as shown by Japanese Patent Publication JP 08281116 A2, filed by Toyota Motor Company, Ltd. (Shinji Tsuji; Mikio Murachi).

The art also shows an awareness of the catalysis of oxidative dehydrogenation of isobutane by lanthanum phosphate and cerium phosphate, as shown by the article Role of Acidic Sites on Metal Phosphates in the Catalytic Oxidation of Isobutane by Y. Takita, K. Kurosaki, T. Ito, Y. Mizuhara and T. Ishihara (Stud. Surf. Sci. Catal., 1994).

SUMMARY OF THE INVENTION

In accordance with the present invention there is provided a catalytic material effective for catalyzing selective oxidation of a gaseous unsaturated hydrocarbon component in the presence of a gaseous oxidant and carbon monoxide. The catalytic material, which optionally may be coated on a carrier member, comprises a phosphated ceria comprised of ceria particles having a phosphate component dispersed thereon. The phosphate component is present in an amount such that, when calculated as elemental phosphorus, it comprises from about 0.1 to 20 percent by weight, preferably from about 1 to 5, more preferably from about 2 to 3 percent by weight, of the phosphated ceria, the weight of the ceria being calculated as $CeO_2$.

One aspect of the present invention provides for the phosphated ceria comprising the catalytic material of the present invention to have a surface area of at least about 10 $m^2/g$, preferably from about 10 $m^2/g$ to 100 $m^2/g$.

In accordance with another aspect of the present invention, there is provided a method of making a phosphated ceria catalytic material effective for catalyzing selective oxidation of a gaseous unsaturated hydrocarbon component in the presence of a gaseous oxidant and carbon monoxide. The method comprises the following steps. (a) Ceria particles and an aqueous solution of a soluble phosphate are combined to form a dispersion of the ceria particles in the solution. (b) The dispersion is heated for a time and at a temperature sufficient to retain on the ceria particles, after separation thereof from the solution, a phosphate component in an amount, calculated as elemental phosphorus, which comprises from about 1 to 20 percent by weight, preferably from about 1 to 5, more preferably, from about 2 to 3 percent by weight, of the phosphated ceria, the weight of the ceria being calculated as $CeO_2$. (c) The resultant phosphated ceria particles are then separated from the solution.

A related method aspect of the invention provides that step (a) above comprises providing the ceria particles in the form of a ceria sol, mixing the ceria sol and the aqueous solution to disperse the ceria sol into the aqueous solution, and step (b) above comprises applying heat to the dispersion obtained in step (a) to evaporate water from the dispersion to dryness, and then calcining the resultant dried material at a temperature of at least about 450° C.

Another related method aspect of the invention provides for step (c) above to comprise filtering the phosphated ceria particles from the solution, and including the further steps of (d) drying the separated particles, and (e) calcining the dried particles at a temperature of at least about 450° C.

In one method aspect of the present invention, the phosphate is selected from the group consisting of monobasic and dibasic phosphate salts and mixtures thereof.

In another method aspect of the present invention, the dispersion is heated at a temperature of from about 40 to 150° C. for a period of from about 1 to 72 hours.

Another aspect of the present invention provides a method for determining the content of gaseous unsaturated hydrocarbon, e.g., olefins, in a gas also containing a gaseous oxidant, e.g., air, and carbon monoxide. The method comprises the following steps. The gas is contacted under oxidizing conditions with a catalytic material comprising a phosphated ceria comprised of ceria particles having a phosphate component dispersed thereon. The phosphate component is present in an amount such that, calculated as elemental phosphorus, it comprises from about 1 to 20 percent by weight, preferably 1 to 5, more preferably, 2 to 3 percent by weight, of the phosphated ceria, with the ceria content calculated as $CeO_2$, and the temperature of the catalytic material is monitored to determine the extent of oxidation taking place at the catalyst.

Other aspects of the present invention will be apparent from the following detailed description of the invention and specific embodiments thereof.

As used herein and in the claims, the following terms have the indicated meanings.

The term "oxidizing conditions" means that the gas stream contains at least sufficient oxidant, e.g., oxygen, to oxidize at least some of the unsaturated hydrocarbon component content of the gas and the temperature at which the gas is contacted with the catalyst is high enough for the catalyzed selective oxidation of the unsaturated hydrocarbons to take place. The defined term also includes conditions where excess oxygen over the stoichiometric amount required to oxidize all the unsaturated hydrocarbon component is present, and further includes conditions where excess oxygen over the stoichiometric amount required to oxidize all the carbon monoxide plus the unsaturated hydrocarbon component in the gas is present.

The term "unsaturated hydrocarbon" or "unsaturated hydrocarbon component" shall mean and include any unsaturated hydrocarbons which are susceptible to oxidation by being contacted with an oxidation catalyst under oxidizing conditions. The term includes alkenes, alkynes, olefins, aromatic compounds and mixtures of two or more thereof.

BRIEF DESCRIPTION OF THE DRAWINGS

FIGS. 2 through 7 are graphs similar to that of FIG. 1, but showing typical conversion curves for the oxidation of propene and carbon monoxide in a gas stream contacted under oxidizing conditions with: (FIG. 2) a comparative platinum on alumina catalytic material, (FIG. 3) a comparative ceria catalytic material, (FIG. 4) a comparative phosphate-treated ceria catalytic material not in accordance with the present invention, (FIG. 5) a phosphated ceria catalytic material in accordance with one embodiment of the present invention, (FIG. 6) a phosphated ceria catalytic material made in accordance with another embodiment of the present invention, and (FIG. 7) a comparative cerium phosphate.

DETAILED DESCRIPTION OF THE INVENTION AND SPECIFIC EMBODIMENTS THEREOF

The catalytic materials of the present invention are effective to catalyze the selective oxidation of certain hydrocarbons in the presence of significant quantities of carbon monoxide (CO). The present invention involves the use of a catalyst system that, upon exposure to a gas or a gas-containing stream comprising an oxidant, e.g., oxygen or air, plus carbon monoxide and one or more hydrocarbon species, including unsaturated hydrocarbon species, and possibly other components such as steam or water vapor, selectively catalyzes the oxidation of unsaturated hydrocarbons while leaving the CO component intact, i.e., unoxidized.

Figure 2:
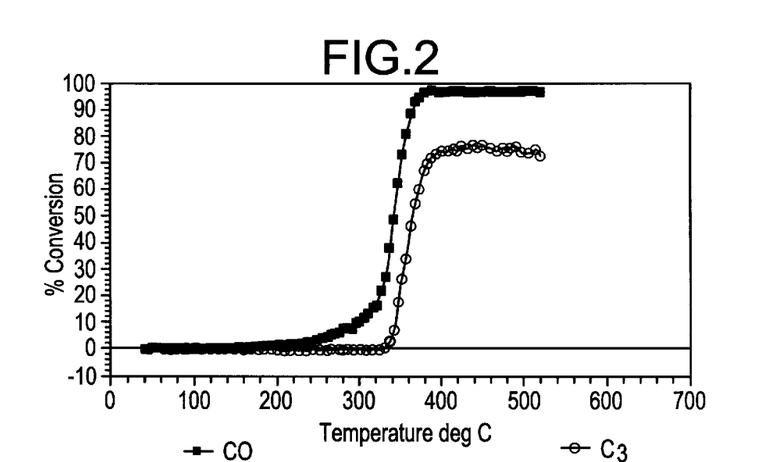

The following species are ranked in their normal order of reactivity for catalytic oxidation; carbon monoxide is more reactive than olefins, which are more reactive than aromatics, which are more reactive than alkanes (paraffins). However, at temperatures of about 200° C. or higher, the reactivities under catalytic oxidation conditions of carbon monoxide and olefins approach each other. This means that for most catalytic materials the temperature at which significant oxidation of unsaturated hydrocarbons, e.g., olefins, begins is very close to the temperature at which the oxidation of carbon monoxide begins. Stated otherwise, the "light off", or conversion curves, which plot the percentage conversion of carbon monoxide and unsaturated olefinic hydrocarbons against the temperature at which the gas stream is introduced to the oxidation catalytic material, are close together, as is illustrated, for example, in FIG. 2. FIG. 2 (which is discussed in more detail below) shows significant oxidation of carbon monoxide as well as oxidation of an unsaturated hydrocarbon, propene, over a large portion of the temperature range.

Under certain circumstances, it is highly advantageous to be able to oxidize unsaturated hydrocarbons such as propene without concomitantly oxidizing carbon monoxide which may be contained in the same gas stream or mixture. For example, one use for the phosphated ceria catalytic material of the present invention is as a component for a hydrocarbon sensor in a motor vehicle exhaust system. The hydrocarbon sensor is placed downstream of a conventional treatment catalyst in order to determine the amount of hydrocarbons which have passed through the treatment catalyst without being oxidized. On the premise that olefins can be used as a surrogate for total hydrocarbons, i.e., the concentration of olefins in the exhaust stream just downstream of the treatment catalyst (which may be a conventional catalytic converter) bears some relation to total hydrocarbons in the exhaust stream, the catalyst of the present invention could be used as a sensor for direct measurement of hydrocarbon content. This is accomplished by measurement of the amount of catalytic activity taking place at the catalytic material disposed on a suitable sensor. By testing for unsaturated hydrocarbons which were not oxidized by the treatment catalyst, the efficacy of the treatment catalyst for removing or reducing the noxious components of combustion waste gas, exhaust gas and other gas streams that contain carbon monoxide and unsaturated hydrocarbons, may be readily determined. Another application for this type of sensor is to estimate the smog potential of ambient air or emissions. Olefins are much more active in creating smog than other hydrocarbons, e.g., paraffins, because olefins are much more reactive than paraffins.

Other uses for the catalytic material of the present invention include, but are not limited to, catalyzing the removal of traces of unsaturated hydrocarbons, e.g., olefins, from CO-containing process streams. Another potential use for the catalytic material of the present invention involves partial oxidation of hydrocarbons to useful chemicals. Examples include, but are not limited to, oxidation of propylene to acrolein/acrylic acid and oxidation of butenes to maleic anhydride.

The catalytic materials of the present invention are phosphated cerias. In one preparation technique, the selective oxidation catalyst of the present invention can be prepared by addition of a phosphate such as a solution of ammonium phosphate to a colloidal ceria and, after taking steps to insure that sufficient phosphate is retained on the ceria particles to attain the purposes of the invention, recovering the solids from the solution, e.g., by evaporating the solution to dryness, and thermally activating the solids. Other preparation techniques include heating an aqueous phosphate solution containing therein a dispersion of ceria particles to adhere a phosphate component to the ceria, and recovering the phosphated ceria, e.g., by filtration and/or centrifugation. In one technique, the dispersion of ceria particles in the aqueous phosphate solution is heated to evaporate the mixture to dryness, thereby depositing substantially the entire phosphate content of the solution on the ceria particles.

Generally, any suitable phosphate may be used to disperse the phosphate component onto the ceria particles. Both monobasic and dibasic phosphates have been used. For example, ceria particles, which may optionally be in the form of colloidal particles of ceria contained in an aqueous solution, may be admixed with a solution of a soluble phosphate, such as a solution of an ammonium phosphate. In some cases, an excess of phosphate component over the amount of phosphate which is to be deposited on the ceria particles will be utilized and, after heating the dispersion of the ceria particles in the phosphate solution for a time and at a temperature sufficient to deposit a desired amount of the phosphate component onto or into the ceria particles, the phosphated ceria particles are separated from the solution. Such separation may be attained by any suitable means, such as filtration, centrifugation or a combination thereof Generally, in order to ensure deposit of a sufficient amount of phosphate onto the ceria particles, the dispersion of the ceria particles in the phosphate solution will be heated at a temperature of at least about 40° C., for example, at a temperature of from about 60 to 150° C., for a period of from about 1 to 72 hours. Generally, at lower temperatures a longer duration of heating is required in order to attain the deposition of an equivalent amount of phosphate.

In another technique, a solution may be prepared containing the total amount of phosphate which is to be deposited on a given quantity of ceria particles and, when that given quantity of ceria particles is mixed with the phosphate solution, the resultant mixture is heated to dryness so that substantially all of the phosphate contained in the solution is deposited on the ceria particles. When using this technique of evaporating a solution to dryness, it is of course necessary to control the quantity of both the ceria particles and the phosphate component in order to attain the desired amount of phosphate component on the ceria particles.

Regardless of the technique employed to deposit the phosphate component on the ceria particles, the dried particles are conveniently thermally activated by being heated in air at a temperature of at least about 400° C., for example, at a temperature of from about 450° C. to 700° C., for a period of from about 0.5 to 20 hours. The thermal activation of the catalytic material may, if desired, be deferred until the catalytic material is placed in use. At that time exposure to a hot gas stream contacted with the catalytic material or other heating of the catalytic material will thermally activate it. However, it is usually preferred to thermally activate the catalytic material prior to use, to avoid an on-stream "break-in" period.

The catalytic material of the present invention utilizes solid particles of ceria, i.e., bulk ceria particles, which are mixed with a solution or other liquid dispersion of a suitable phosphate component. Aqueous solutions of ammonium phosphate, both monobasic and dibasic ammonium phosphate, have been successfully used as the phosphate component.

The unique selectivity of the catalytic materials of the present invention for catalyzing the oxidation of unsaturated hydrocarbons in the presence of carbon monoxide may be demonstrated by testing a portion of the catalytic material either as a powder, or coated onto a carrier such as a ceramic honeycomb-type monolith carrier. The catalytic material is placed in a catalytic reactor through which is passed dilute concentrations of hydrocarbon and carbon monoxide. For test purposes, the hydrocarbon may consist of an approximately equal mixture of propene and propane or, alternatively, only propene need be fed as the hydrocarbon. The carbon monoxide concentration may be approximately twice the hydrocarbon concentration for test purposes, and the reactive stream may be dry, or alternatively, water vapor (steam) may be added. Excess oxygen, as air, may be added as the oxidant.

A typical prior art oxidation catalyst, platinum on alumina, is not selective for hydrocarbons or olefins. The selectivities of ceria, cerium phosphate and phosphate-treated ceria not in accordance with the present invention are better, but still only very poorly selective or of low activity, as will be demonstrated below. In stark contrast, the phosphated ceria of the present invention exhibits complete oxidation of olefin prior to any net observable oxidation of carbon monoxide. Thus, this catalyst is selective for hydrocarbon (olefin) oxidation in the presence of carbon monoxide and this attribute of favoring hydrocarbon oxidation with no or low carbon monoxide oxidation is believed to be unique to the phosphated ceria of the present invention.

In FIGS. 1 through 5, the conversion curve for carbon dioxide is indicated by its chemical symbol "CO", and the conversion curve for propene is indicated by "$C_3$".

Figure 1:
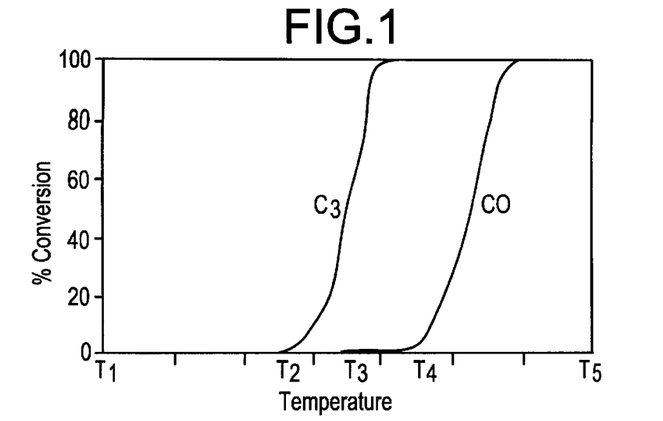
FIG. 1 is a graph showing percent conversion versus temperature curves ("conversion curves") for oxidation of, respectively, $C_3$ hydrocarbons and carbon monoxide for a theoretical, perfectly selective catalytic material.

For applications involving moderate to high temperatures, e.g., for temperatures of the gas stream immediately prior to contacting the catalytic material of from about 200° C. to about 600° C., e.g., from about 250° C. to about 580° C., ideal selectivity for oxidation of unsaturated hydrocarbons in preference to carbon monoxide is illustrated by the theoretical conversion curves of FIG. 1. In FIG. 1, the temperature at which the gas stream being treated is contacted with the catalytic material is shown on the horizontal axis as $T_1$ through $T_5$, with $T_1$ being the lowest temperature and each successive temperature ($T_2$, $T_3$, etc.) being higher than the one preceding it, with the highest temperature being $T_5$. As shown by FIG. 1, the percent conversion of the unsaturated hydrocarbon increases with increasing temperature while, over a relatively large temperature range, up to about temperature $T_4$, there is substantially no conversion or oxidation activity for the carbon monoxide. Starting at about temperature $T_2$, conversion of the unsaturated hydrocarbon $C_3$ commences and the hydrocarbon is substantially 100% converted by the time temperature $T_3$ is reached, whereas significant oxidation of carbon monoxide does not commence until a temperature in excess of temperature $T_4$ is attained. FIG. 1 thus illustrates theoretically perfect selectivity of the catalyst, inasmuch as 100% of the hydrocarbon is oxidized before substantially any of the carbon monoxide is oxidized.

Figure 5:
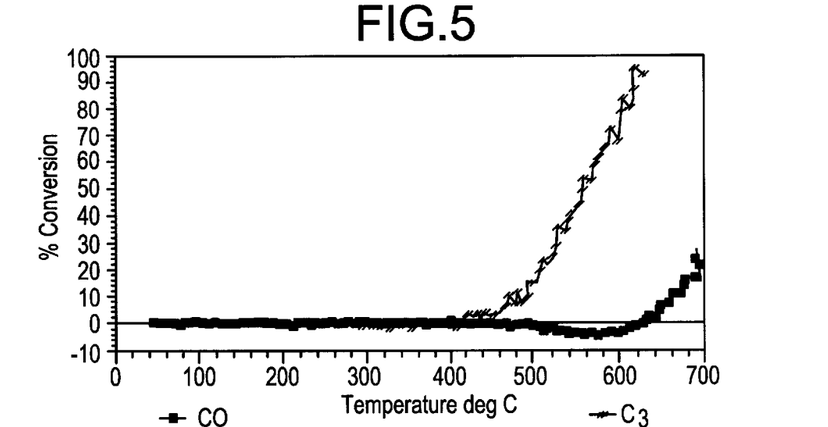

A close approach to the ideally selective conversion curves of FIG. 1 is attained by catalytic materials in accordance with the present invention, for example, see the conversion curve of FIG. 5, discussed in more detail below. While pre-heating the gas stream was the technique used in generating the data for the examples, in other situations the catalyst itself may be heated in addition to, or in lieu of, pre-heating the gas stream. In still other situations, for example, in treating engine exhaust streams, the gas stream may already be at an elevated temperature high enough for catalytic oxidation of the carbon monoxide.

The catalytic material of the present invention may be utilized as a powder which is packed within a tube or other suitable vessel through which the gas to be treated is flowed. In such case, the catalytic material may be supported between gas-permeable retention means such as screens, beds of particulate frit, glass or steel wool, or the like. Alternatively, the unsupported catalyst may be pressed or extruded or otherwise formed into the shape of beads, pellets, extrudates or the like, or it may be coated on a suitable carrier such as alumina beads or on the walls of the gas flow passageways of a honeycomb-type catalyst carrier made of a suitable ceramic-like material, e.g., cordierite. Honeycomb-like carriers are usually formed as a cylindrical monolith having a plurality of fine, parallel gas flow passages extending therethrough, the walls of which passages are coated with a slurry containing the catalytic material and thereafter dried and calcined, as is well known to those skilled in the art. For being pressed or otherwise formed into a particular shape and for being coated onto a carrier, a binder and/or other suitable adjunct materials may be added to the catalytic material powder.

Figure 6:
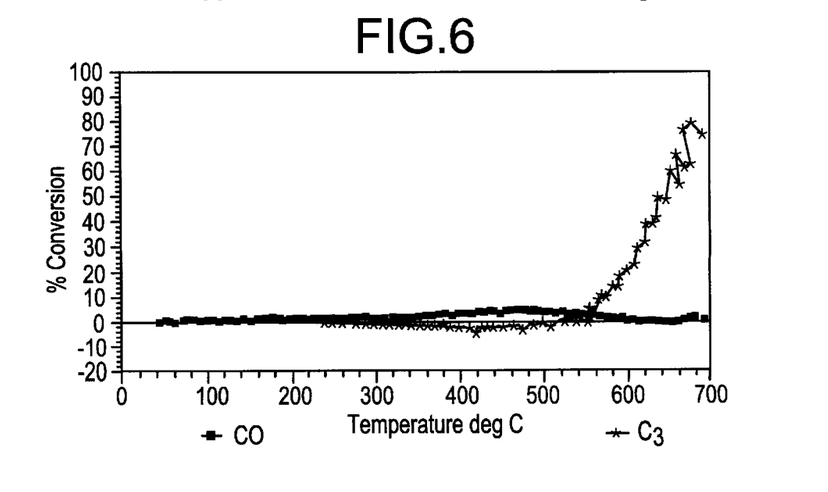

The catalytic material of the present invention may also be deposited as a coating on a sensor used to detect the quantity of hydrocarbons in a gas stream, as is described below in connection with FIG. 6.

EXAMPLE 1

Preparation of Materials

A. Phosphated Ceria 20 g of a ceria sol (20 wt. % solution obtained from Aldrich Chemical Company of Milwaukee, Wis. was weighed out into a glass beaker. 60 g of water was added to this solution and stirred.

4.79 g of 1 M dibasic ammonium phosphate (($NH_4$)$_2HPO_4$) aqueous solution was weighed into a beaker. Approximately 20 g of water was added and mixed. This solution was added slowly to the ceria solution. Once all the phosphate was added, the mixture was placed in an evaporating dish, and low heat was applied to evaporate the liquid.

The dry mixture was first placed inside an oven at approximately 100° C., and then calcined at 1000° F. (538° C.) for approximately two hours. The resultant phosphated ceria catalytic material powder contained 3.3 percent by weight of phosphate component, calculated as elemental phosphorus.

B. Platinum on Alumina

High surface area gamma alumina was impregnated to incipient wetness with a solution of a soluble platinum salt such that the final concentration of platinum metal is approximately 0.2 wt % of the combined weight of platinum and ceria. The resulting material was dried and then calcined at 600° C. The surface area of the resulting material was greater than about 150 $m^2$/g and the particle size after ball milling was not more than about 5 microns in diameter.

C. Cerium Oxide

Cerium oxide powder was purchased from Aldrich Chemical Company of Milwaukee, Wis.

D. Phosphate-Treated Cerium Oxide Powder 0.24 g of ammonium phosphate, monobasic was dissolved in 50 ml water. To this solution was added 8 g of cerium oxide powder. The resulting slurry was stirred for 15 minutes and then filtered and washed. The separated solids were dried at 100° C.

E. Applying the Catalytic Material as a Coating on a Honeycomb-Like Monolith Carrier Four grams (dry basis) of the catalytic material powder obtained from any of parts B through D of this Example 1 was combined with enough water to make a 45% by weight solids slurry. (The powders of Parts B, C and D of this Example were used to coat monoliths; the powder of Example A was tested as a powder.) The resulting slurry was homogenized with a magnetic stirrer and then transferred to a one-ounce (liquid) capacity plastic vial fitted with a snap cap. A weighed ceramic (cordierite) honeycomb-type monolith carrier in the shape of a cylinder with dimensions 1 inch (2.54 cm) high×¾ inch (1.91 cm) in diameter and a cell density of 400 cells per square inch (62 cells per square centimeter) was placed into the plastic vial. (The "cell density" refers to the number of parallel gas-flow channels per square inch of end face of the carrier.) The vial was inverted several times to ensure that the slurry passes through all the channels of the monolith to coat the walls thereof. The monolith was then removed from the vial and excess slurry was removed with an air knife. The monolith was weighed to determine if the appropriate amount of coating had been applied. After the coating weight was found to be acceptable, the monolith was dried at 120° C. Then the monolith was placed in a crucible and the crucible was placed into a furnace. The temperature of the furnace was raised to 550° C. and held at that temperature for two hours. The crucible was then removed from the furnace and allowed to cool to room temperature. All coated-monolith samples received the foregoing treatment. The cooled monolith was weighed and the weight of dry coating of catalytic material was determined by subtracting the weight of the uncoated monolith from the weight of the coated monolith. The weight (dry basis) of the coating of the catalytic material on the monoliths was 0.6 gram (which is equivalent to 2.0 grams per cubic inch of volume of the coated monoliths).

F. Utilizing the Catalytic Material as a Powder

When the catalytic material was tested as a powder, a quantity of the catalytic material powder to be tested (that obtained from part A of this Example 1) was supported within the reactor tube of the test apparatus on a bed of quartz frit.

EXAMPLE 2

Catalyst Performance Testing

The catalyst performances reported in the following examples were all evaluated using a laboratory test reactor and the following procedure. A gas stream containing the reactants of interest (an oxidant, carbon monoxide and hydrocarbons comprising a mixture of propane and, as the unsaturated hydrocarbon, propene) at the desired concentrations was generated. The gas stream was then heated to the desired temperature, and passed over the catalyst (either coated on a monolith or as a powder) contained in a quartz tube at the desired temperature. The concentrations of hydrocarbon and carbon monoxide both upstream and downstream of the catalyst were monitored using hydrocarbon, carbon monoxide and carbon dioxide sensors obtained from Rosemount Analytical, Inc., La Habra, Calif.

Approximately 0.6 gram of catalytic material was coated, as described above, onto a cordierite monolith in the form of a cylinder approximately 1 inch long and ¾ inch in diameter. The cylindrical side of the monolith was wrapped with a belt of ceramic "felt" to prevent gas by-pass around the side of the monolith, i.e., to insure that all the gas flows through the gas-flow channels of the monolith to contact the catalytic material coated on the walls thereof. The wrapped monolith was then inserted into a quartz reactor tube. The quartz reactor tube is placed in a programmable tube furnace whose temperature is controlled by a thermocouple in a quartz thermowell suspended just above the catalyst being tested.

Gases were fed to the reactor tube using mass flow controllers. A static mixer was used to insure good mixing of the feed gases and a syringe pump was used to feed water to a vaporizer to allow inclusion of steam in the feed stream, if desired. The combined feed gases were passed over the catalyst at 5–6 psig.

At the exit to the reactor, any water vapor was removed from the exit gas stream by passing the exit gas stream through a mini gas sampling system (MG-1220-S1-10) apparatus sold under the trademark PERMA PURE by Perma Pure Inc. of Toms River, N.J. This apparatus comprises a water-permeable membrane through which only the water content of the tested gas stream passes for removal by a nitrogen carrier gas. The dried exit gas stream was then directed to three different Rosemount analyzers: one to analyze for total hydrocarbon content, one for carbon monoxide content and one to analyze for carbon dioxide content.

In a typical experiment, a "conversion curve" (often referred to as a "light-off" curve) of feed species versus temperature was generated. The conversion was obtained by raising the temperature of the reactor in a controlled linear fashion from ambient or near ambient to 500 to 700° C. and noting the change, if any, of reactant concentration in the product gas as a function of temperature. Typically, one analytical result was recorded every 20 seconds. The conversions (oxidation) of unsaturated hydrocarbon and carbon monoxide were calculated by measuring the differences in, respectively, the hydrocarbon and carbon monoxide contents of the feed (to the catalyst) and exit (from the catalyst) test gas streams. These conversions were plotted versus temperature of the inlet gas stream to the catalyst to generate a conversion curve. Percent conversion for any reactant species is defined as the difference between the concentration of the species in the feed gas to the catalyst and the concentration of the species in the exit gas from the catalyst, divided by the concentration of the species in the feed gas, all multiplied by 100.

Typical Reactor Conditions

1. Flow Rates

Total Dry Flow (excluding water vapor) is 3000 cubic centimeters per minute ("cc/min") at standard temperature and pressure ("STP"), i.e., 21° C. and 1 atmosphere, and includes an air flow of 75 cc/min at STP.

Space Velocity: 25,000 per hour at STP.

Reactor Condition A: Total wet flow (including water vapor): 3408 cc/min at STP.

Reactor Condition B: No added moisture

2. Temperature

Temperature Ramp Rate: 15° C./minute

3. Composition of Test Gas

Carbon Monoxide Concentration: 1700 ppm by volume

Reactor Condition A: Propane concentration: 472 ppm volume ($C_1$ basis) Propene concentration: 432 ppm volume ($C_1$ basis) Nitrogen: balance The propane is inert to the oxidation reaction, as demonstrated by simple experiments. In experiments in which an approximately 50:50 mixture of propane and propene were fed concurrently to a suitable oxidation catalyst under oxidizing conditions, the oxidation of hydrocarbons levels out at approximately 50 percent. In subsequent experiments where only propene is fed to the catalyst under oxidizing conditions, substantially all the propene is oxidized, which is consistent with the oxidation behavior associated with 50 percent of the propane-propene mixture. These results are consistent with the general reactivity of, respectively, olefins and saturated hydrocarbons, wherein olefins are much more reactive at a given set of oxidation conditions than are paraffins, i.e., saturated hydrocarbons.

Reactor Condition B: Propane concentration: none Propene concentration: 900 ppm volume ($C_1$ basis)

Specifics of the Tests

The catalytic material powders of comparative Examples 3, 4 and 5 were tested as coatings on the monolithic honeycomb-type carriers, as described above. The catalytic material of Example 6 was tested as a powder by placing about 0.1 to 0.2 g of the powder in an approximately 14 mm inside diameter quartz reactor tube containing a quartz frit in the middle region of the tube.

In all cases, the rest of the test apparatus and reactor flows were as described above under the heading "Catalyst Performance Testing" in Example 2.

The results of performance testing of these catalytic materials were obtained as described above in Example 2. Resulting light-off curves for the catalytic materials tested are shown in FIGS. 2 through 5.

Test Results

The following examples describe the test results.

Comparative Example 3

Platinum on Alumina

The platinum on alumina catalytic material obtained from Part B of Example 1 is a typical precious metal oxidation catalyst. When tested under Reactor Condition A of Example 2 as a coating on a monolith carrier, this material catalyzed the oxidation of the carbon monoxide at a lower temperature than that at which oxidation of the propene took place. The test results are plotted as conversion curves in FIG. 2, which shows that clearly discernible oxidation of carbon monoxide occurred at a temperature of from about 210° to 310° C., whereas discernible oxidation of the unsaturated hydrocarbon did not commence until a temperature of about 320° C. was attained. This means that at all temperatures necessary for hydrocarbon oxidation, carbon monoxide oxidation will occur as well. Therefore, this is a non-selective catalyst for oxidation of hydrocarbon in the presence of carbon monoxide.

Comparative Example 4

Cerium Oxide Powder

Figure 3:
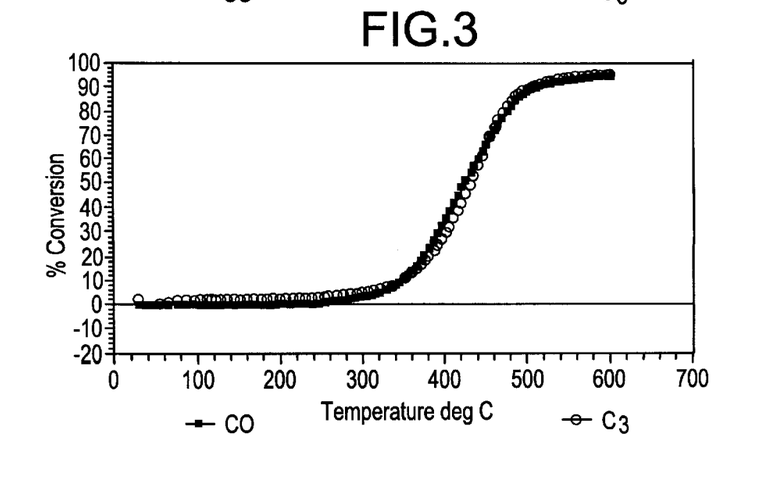

The catalytic material obtained from Part C of Example 1, i.e., cerium oxide powder, was tested as a coating on a monolith under Reactor Condition B of Example 2, and the resultant conversion curves are shown in FIG. 3. As shown by FIG. 3, the olefin (propene) and carbon monoxide oxidize at essentially the same temperature. This demonstrates that ceria alone is a non-selective catalyst for the oxidation of olefins in the presence of carbon monoxide.

Comparative Example 5

Phosphate-Treated Cerium Oxide Powder

Figure 4:
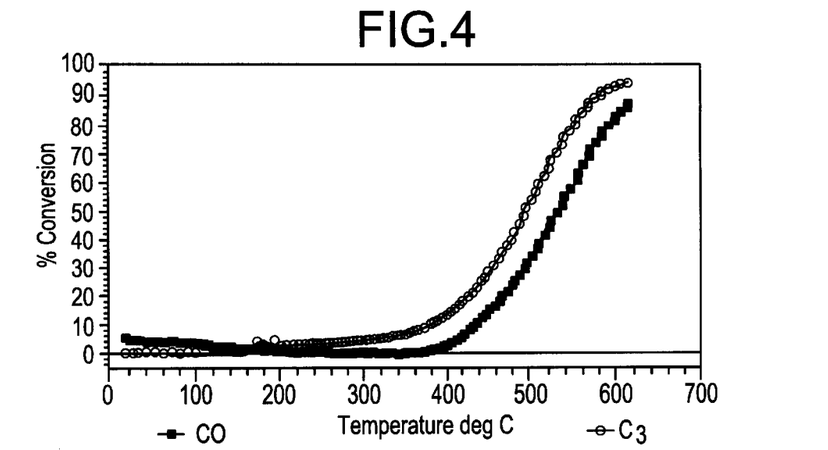

The phosphate-treated cerium oxide catalytic material obtained from Part D of Example 1 was tested as a coating on a monolith under Reactor Condition B of Example 2, and the resultant conversion curve is illustrated in FIG. 4. FIG. 4 shows that although oxidation of propene commenced at a temperature of about 200° C., and that of carbon monoxide did not commence until a temperature of over about 390° C., the amount of propene oxidation in that temperature range attained as much as 10% only at the upper end of that temperature range, and thereafter significant carbon monoxide oxidation occurred with only a slight preference for oxidation of the olefin. Although propene oxidation occurred at a lower temperature than did oxidation of carbon monoxide, the reactivities of the propene and the carbon monoxide are so close that a highly selective oxidation of olefin to high conversion levels in the presence of carbon monoxide is not possible.

EXAMPLE 6

Phosphated Ceria

Phosphated ceria in accordance with one embodiment of the present invention, as obtained from Part A of Example 1, was tested as a powder utilizing Reactor Condition A of Example 2. FIG. 5 shows the resultant conversion curves obtained and it will be noted that the catalytic behavior of phosphated ceria in accordance with this embodiment of the present invention was very distinct from that of the Comparative Examples 3–5. As shown in FIG. 5, at temperatures between 400° and 500° C., low percentage conversion of propene was observed. The propene conversion then increases rapidly and approaches 100% at approximately 600° C. Throughout this temperature range no net conversion of CO was observed. The first indication of CO conversion was observed above about 625° C., by which point 100% propene conversion had been achieved.

Therefore, the catalytic material catalyzed the oxidation of propene in the presence of CO in a perfectly selective manner.

EXAMPLE 7

Phosphated Ceria 20 g of a high surface area ceria was mixed with 225 ml of 1M $(NH_4)_2HPO_4$ solution. The mixture was placed in an autoclave and heated at 90° C. with stirring for 48 hours. The resulting product was filtered and washed. The final product contained 2.7 weight percent phosphate component calculated as elemental phosphorus and was coated onto a monolith as described above and the coated monolith was tested utilizing reaction conditions A of Example 2. The test data were plotted to provide the conversion curves of FIG. 6. These curves show that this test material showed activity and selectivity comparable to that of Example 6, except that significant oxidation of the propene started at about 550° C., which is about 100° C. higher than in the case of Example 6.

Comparative Example 8

Cerium Phosphate

As a control experiment, cerium phosphate was prepared according to the following literature procedure and tested as a catalytic material powder, utilizing Reactor Conditions A of Example 2.

150 ml of 6M $H_3PO_4$ was put in a 500 ml round-bottom flask and was set up for reflux. This solution was heated to 95–100° C.

62 ml of cerium sulfate solution (0.25 N $Ce(SO_4)_2$ in $H_2SO_4$) was added to approximately 100 ml water. This solution was added dropwise to the phosphoric acid solution. Immediate precipitation occurred. Approximately half of the total solution was added since there was a very large solid content in the solution. The reaction was continued for about 3 hours. The resulting product remained in its mother liquor over the weekend. The final cerium phosphate product was filtered and washed.

Figure 7:
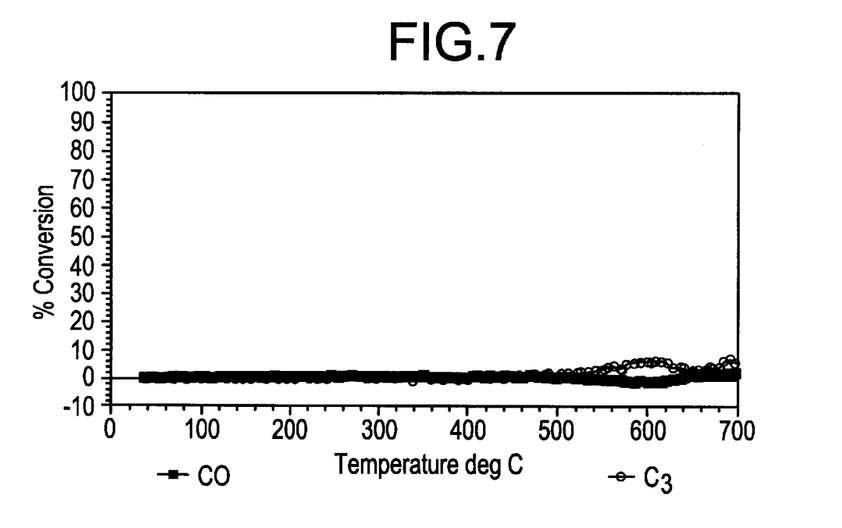

This material was estimated to have a P:Ce atomic ratio of 2:1 that would correspond to 19.7 percent by weight phosphate component calculated as elemental phosphorus. The data developed by testing this material were plotted as conversion curves in FIG. 7. As shown by FIG. 7, this material showed very low propene conversion (~5% propene conversion) at about 600° C. and substantially no carbon monoxide oxidation. Although the selective oxidation of propene in the presence of carbon monoxide was attained using phosphated ceria catalytic materials of the present invention containing as much as 20 percent by weight of phosphate component, the propene conversion attained with such high phosphate component levels was quite low, about 5% as indicated above. (Unless otherwise stated, all references to percent by weight phosphate component are on the basis that the phosphate component is calculated as elemental phosphorus.) Without wishing to be bound by any theory, it appears that at the higher ranges of phosphate component content, a concomitant reduction in surface area may account for the reduced catalytic activity. The high phosphate-containing materials are nonetheless selective in that they promote (limited) oxidation of the unsaturated hydrocarbon, but do not promote oxidation of the carbon monoxide. Nonetheless, in order to attain desirable high conversions (oxidation) of the unsaturated hydrocarbons, including 100 percent oxidation of unsaturated hydrocarbons with substantially no carbon monoxide oxidation, the preferred phosphate component range is 1 to 5 weight percent, and the most preferred phosphate component range is 2 to 3 weight percent.

Generally, good results have been attained wherein the surface area of the phosphated ceria of the present invention is at least about 10 square meters per gram ("$m^2/g$") after the ceria is phosphated. It has been found that, with a post-phosphated surface area of less than about 10 $m^2/g$, catalytic activity is unsatisfactory in that only a very small amount of the unsaturated hydrocarbon will be oxidized, although catalyst selectivity for oxidation of unsaturated hydrocarbons is good. Good results with respect to both activity and selectivity have been obtained with phosphated ceria catalytic materials of the present invention having surface areas of about 50 to 80 $m^2/g$ after being phosphated. Generally, a surface area after being phosphated of at least 25 $m^2/g$ and, preferably, 25 to 100 $m^2/g$, is preferred. Surface areas as described here and in the claims is as measured by the Brunauer-Emmett-Teller ("BET") technique.

Figure 8:
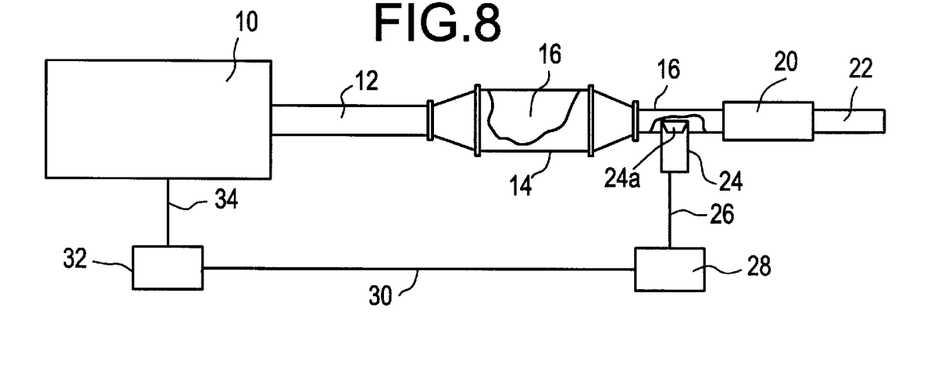
FIG. 8 is a schematic diagram showing one environment of use of the selective catalytic material of the present invention in the exhaust line of an engine fueled by a hydrocarbonaceous fuel such as gasoline, diesel oil or natural gas.

Referring now to FIG. 8, there is shown a schematic illustration of one environment of use of the selective catalytic material of the present invention. In this case, the catalytic material is disposed in the exhaust conduit of an internal combustion engine 10, from which engine exhaust is transmitted by exhaust conduit 12 to a catalytic converter 14 which is partially broken away to show a treatment catalyst 16 disposed therein. Treatment catalyst 16 may comprise a monolithic carrier, the gas flow channels of which (not shown) are disposed parallel to the longitudinal axis of exhaust conduit 12. The walls of the gas flow channels are coated with a suitable catalytic material of any known type. The catalytic material utilized in the treatment catalyst may be an oxidation catalyst, such as a platinum-on-alumina support, or it may be the type of catalyst known to those skilled in the art as a three-way conversion catalyst. A three-way conversion catalyst contains a catalytic material which promotes substantially simultaneous oxidation of hydrocarbons and carbon monoxide and reduction of nitrogen oxides. After passing through treatment catalyst 16, the treated exhaust gases pass through a transfer conduit 18, then through a conventional sound-deadening muffler 20, for discharge to the atmosphere via an exhaust pipe 22. The arrangement thus far described is conventional, showing the interposition of a catalytic converter into the exhaust gas discharge of, e.g., an automobile or diesel engine, in order to treat the exhaust gases to reduce the noxious pollutant content thereof prior to discharge to the atmosphere.

Transfer conduit 18 is broken away in FIG. 8 to better show the insertion of a sensor 24 therewithin so that a portion at least of sensor 24 contacts the treated exhaust gases exiting from treatment catalyst 16. Sensor 24 is connected via a first lead 26 to a sensor electronics package 28, which is in turn connected by a second lead 30 to engine control unit 32. Engine control unit 32 is connected by a third lead 34 to engine 10.

Sensor 24 has coated thereon an adherent layer of a phosphated ceria catalytic material 24a in accordance with an embodiment of the present invention.

In the known manner, sensor 24 may be heated by, e.g., a platinum electric resistance wire (not shown) which serves both to control the temperature and to transmit temperature data showing the additional heating of catalytic material 24a by the oxidation reaction it catalyzes. The temperature increase reflecting the amount of unsaturated hydrocarbon oxidation carried out at catalytic material 24a is transmitted to a transducer (not shown) from which transducer information is transmitted to first lead 26, thence to sensor electronics package 28. This information concerning the amount of unsaturated hydrocarbon oxidation taking place at catalytic material 24a, optionally used in conjunction with other information concerning the conditions in the exhaust stream being treated, indicates the quality of the performance of treatment catalyst 16. That information may be relayed via second lead 30 to engine control unit 32, which transmits an appropriate operating signal via third lead 34 to engine 10, in order to adjust operation thereof. For example, in response to the signal from engine control unit 32, the air/fuel ratio of the fuel supply to the engine may be adjusted in order to enhance performance of treatment catalyst 16. If poor performance persists, catalytic converter 14 may have to be replaced.

While the invention has been described in detail with respect to specific preferred embodiments thereof, it is to be understood that upon a reading of the foregoing description, variations to the specific embodiments disclosed may occur to those skilled in the art and it is intended to include such variations within the scope of the appended claims.

What is claimed is:

1. A catalytic material effective for catalyzing selective oxidation of a gaseous unsaturated hydrocarbon component in the presence of a gaseous oxidant and carbon monoxide, the catalytic material comprising a phosphated ceria comprised of ceria particles having a phosphate component dispersed thereon in an amount such that the phosphate component, calculated as elemental phosphorus, comprises from about 0.1 to 20 percent by weight of the phosphated ceria, the weight of the ceria being calculated as $CeO_2$.

2. The catalytic material of claim 1 wherein the phosphate component comprises from about 1 to 5 percent by weight of the phosphated ceria.

3. The catalytic material of claim 1 wherein the phosphate component comprises from about 2 to 3 percent by weight of the phosphated ceria.

4. The catalytic material of claim 1, claim 2 or claim 3 coated on a carrier member.

5. The catalytic material of claim 1, claim 2 or claim 3 wherein the phosphated ceria has a surface area of at least about 10 $m^2/g$.

6. The catalytic material of claim 5 wherein the phosphated ceria has a surface area of from about 10 $m^2/g$ to 100 $m^2/g$.

7. A catalytic material effective for catalyzing selective oxidation of a gaseous unsaturated hydrocarbon component in the presence of a gaseous oxidant and carbon monoxide, the catalytic material comprising a phosphated ceria comprised of ceria particles having a phosphate component dispersed thereon in an amount such that the phosphate component, calculated as elemental phosphorus, comprises from about 1 to 5 percent by weight of the phosphated ceria, the weight of the ceria being calculated as $CeO_2$, and the ceria particles after being phosphated having a surface area of from about 10 to 100 $m^2/g$.

8. A method of making a phosphated ceria catalytic material effective for catalyzing selective oxidation of a gaseous unsaturated hydrocarbon component in the presence of a gaseous oxidant and carbon monoxide, the method comprising: (a) combining ceria particles and an aqueous solution of a soluble phosphate to form a dispersion of the ceria particles in the solution, (b) heating the dispersion for a time and at a temperature sufficient to retain on the ceria particles, after separation thereof from the solution, a phosphate component in an amount, calculated as elemental phosphorus, which comprises from about 0.1 to 20 percent by weight of the phosphated ceria, the weight of the ceria being calculated as $CeO_2$, and (c) separating the resultant phosphated ceria particles from the solution.

9. The method of claim 8 wherein the phosphate component comprises from about 1 to 5 percent by weight of the phosphated ceria.

10. The method of claim 8 wherein the phosphate component comprises from about 2 to 3 percent by weight of the phosphated ceria.

11. The method of claim 8 wherein the phosphate is selected from the group consisting of monobasic and dibasic phosphate salts and mixtures thereof.

12. The method of claim 8 wherein step (b) comprises heating the dispersion at a temperature of from about 40 to 150° C. for a period of from about 1 to 72 hours.

13. The method of claim 8 wherein step (b) comprises applying heat to the dispersion obtained in step (a) to evaporate water from the dispersion to dryness, and then calcining the resultant dried material at a temperature of at least about 450° C.

14. The method of claim 13 wherein step (a) comprises providing the ceria particles in the form of a ceria sol, and mixing the ceria sol and the aqueous solution to disperse the ceria sol into the aqueous solution.

15. The method of claim 8 wherein step (c) comprises filtering the phosphated ceria particles to separate them from the solution and washing the separated particles, and including the further steps of (d) drying the separated particles, and (e) calcining the dried particles at a temperature of at least about 450° C.

16. A method for determining the content of gaseous unsaturated hydrocarbon in a gas also containing a gaseous oxidant and carbon monoxide comprises:

contacting the gas under oxidizing conditions with a catalytic material comprising a phosphated ceria comprised of ceria particles having a phosphate component dispersed thereon in an amount such that the phosphate component, calculated as elemental phosphorus, comprises from about 0.1 to 20 percent by weight of the phosphated ceria, with the ceria content calculated as $CeO_2$; and monitoring the temperature of the catalytic material to determine the extent of oxidation taking place at the catalyst.

17. The method of claim 16 wherein the oxidant comprises air.

18. The method of claim 16 wherein the unsaturated hydrocarbon comprises one or more olefins.

19. The method of claim 16, claim 17 or claim 18 wherein the phosphate component comprises from about 1 to 5 percent by weight of the phosphated ceria.

20. The method of claim 19 wherein the phosphate component comprises from about 2 to 3 percent by weight of the phosphated ceria.

* * * * *